(12) United States Patent
Newell

(10) Patent No.: US 8,273,298 B2
(45) Date of Patent: Sep. 25, 2012

(54) BODY ODOR DETECTION DEVICE

(76) Inventor: Thomas L. Newell, Cumming, GA (US)

( * ) Notice: Subject to any disclaimer, the term of this patent is extended or adjusted under 35 U.S.C. 154(b) by 35 days.

(21) Appl. No.: 12/460,728

(22) Filed: Jul. 23, 2009

(65) Prior Publication Data

US 2010/0021341 A1   Jan. 28, 2010

Related U.S. Application Data

(60) Provisional application No. 61/135,758, filed on Jul. 23, 2008.

(51) Int. Cl.
*G01N 33/00* (2006.01)
(52) U.S. Cl. ............... 422/83; 422/84; 422/85; 422/86; 422/87; 422/88
(58) Field of Classification Search ............... 422/83, 422/84, 85, 86, 87, 88
See application file for complete search history.

(56) References Cited

U.S. PATENT DOCUMENTS 4,472,353 A * 9/1984 Moore ..................... 422/401
5,322,797 A * 6/1994 Mallow et al. ............. 436/106
* cited by examiner

*Primary Examiner* — Sam P Siefke
(74) *Attorney, Agent, or Firm* — Harry I. Leon; Vivian L. Steadman

(57) ABSTRACT

A device for detecting human body odors produced from ammonia and amino acids—chemicals naturally excreted through the skin and sweat glands. Unless eliminated, such odors can alert game animals to a hunter's presence. Worn on the exterior of odor-absorbing clothing, the device includes both a packet and an indicator chemical sensitive to extremely low concentrations of nitrogen-containing compounds. The packet defines first and second openings which, in use, are directed away from and toward the wearer's body, respectively. Affixed to the packet, a transparent tape forms an airtight window through which one can continually view the indicator chemical, held in place within the first opening by the tape's adhesive backing. Accessible only to substances which pass through the wearer's clothing and then into the packet's interior via the second opening, the indicator chemical undergoes a permanent color change, once odor-producing chemicals begin to break through the clothing.

4 Claims, 2 Drawing Sheets

Fig. 1
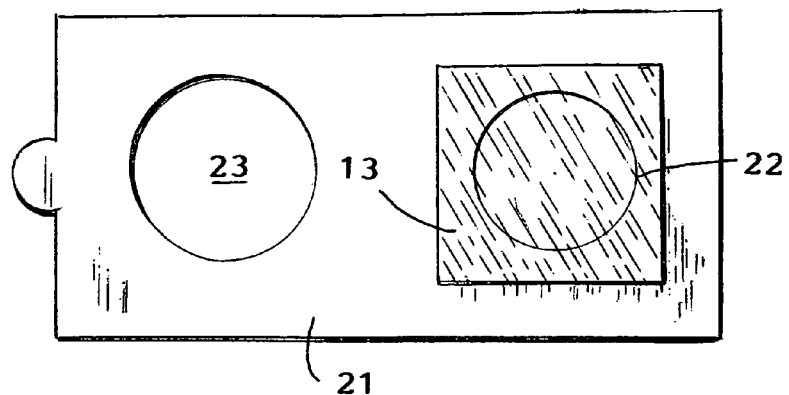
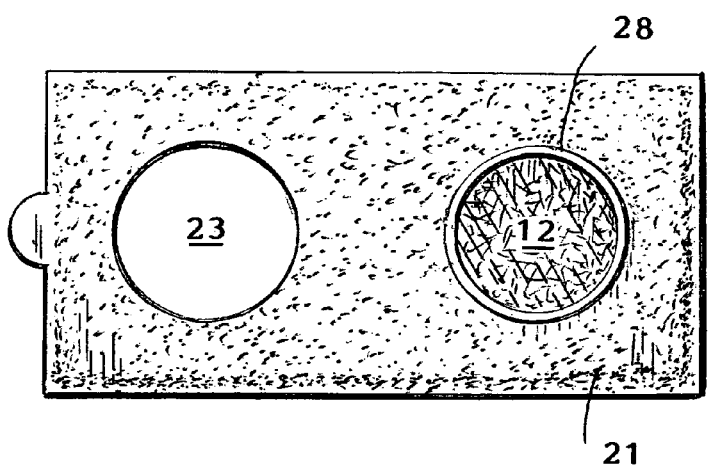
Fig. 2
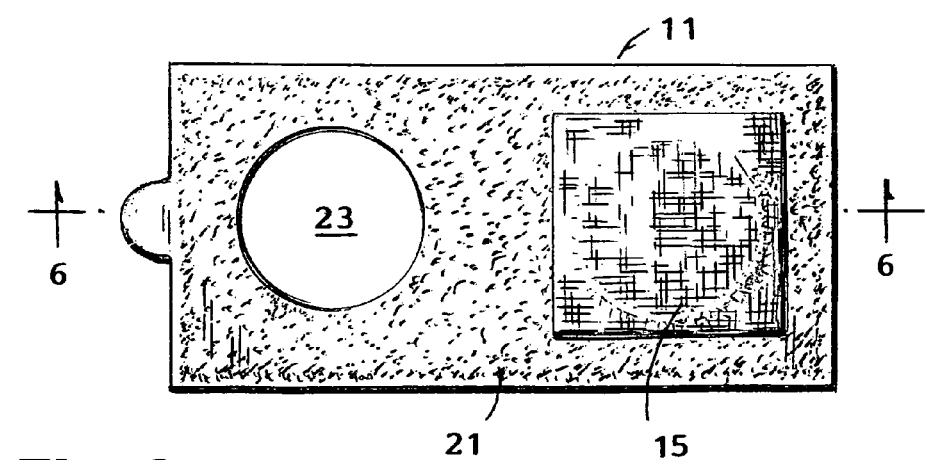
Fig. 3

Fig. 4
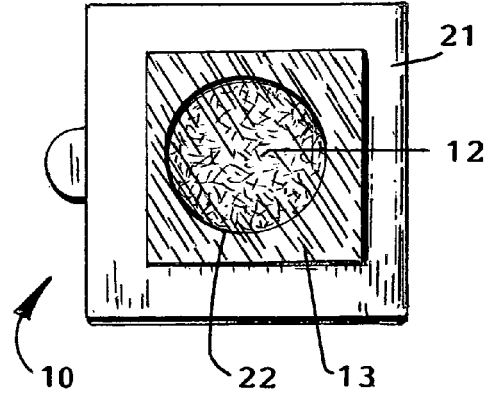
Fig. 5
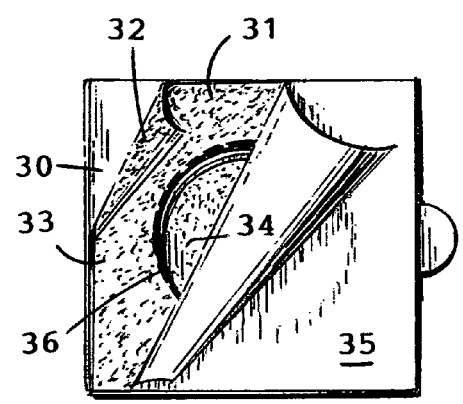
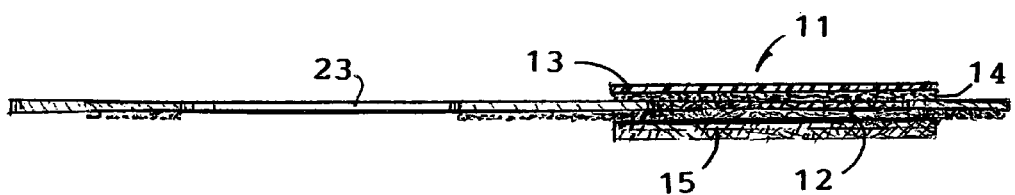
Fig. 6

BODY ODOR DETECTION DEVICE

CROSS REFERENCE TO RELATED APPLICATION

This application is a non-provisional application of the earlier filed provisional application Ser. No. 61/135,758, filed Jul. 23, 2008, and claims the benefit of the priority of the filing date of Jul. 23, 2008, pursuant to 35 U.S.C. Sec. 119(e).

FIELD OF THE INVENTION

The present invention relates to devices for indicating the presence of airborne chemicals and especially to such devices which change color when exposed to compounds present in human body odor.

BACKGROUND OF THE INVENTION

It is unavoidable that humans emanate odor. This odor is produced by a chemical mixture, excreted through the skin and sweat glands, which contains ammonia and amino acids. It is well known that wild game animals have a keenly developed sense of smell and can readily distinguish odors that are not indigenous to their natural habitat. Hunters seeking to get into close proximity to game animals have sometimes tried special clothing in an attempt to either mask or absorb their natural body odor. In the related prior art, Sesselmann, U.S. Pat. No. 5,539,930, discloses a system of special clothing for hunters designed to absorb body odor. Fore, U.S. Pat. No. 5,891,391, discloses a clothing deodorizer for deer hunters.

Devices designed for personal protection against environmental hazards caused by ammonia fumes are also well known in the prior art. However, none of these devices is suitable for detecting gaseous ammonia when it is present in only parts per billion, which is the order of magnitude of those concentrations of ammonia found in human body odor. The American Gas Co., for example, markets ammonia detectors used for personal protection. When exposed to gaseous ammonia in the sensitivity range of 25 ppm for five minutes, the indicator chemicals in them change color from yellow to blue. However, when American Gas & Chemical Co. detectors were tested to see if they could be used to detect ammonia and amino acids at the concentrations at which they are found in human body odors, no change of color occurred. Further, after these detectors had been exposed to high concentrations of ammonia which changed the color of their indicator chemicals to blue and after they were then removed from these high concentrations, their color changed back to yellow.

Like the indicator chemicals in the American Gas & Chemical Co. detectors, those used in the paint or coating compositions disclosed by Mallow et al., U.S. Pat. Nos. 5,183,763 and 5,322,797 (hereinafter "Mallow"), when incorporated into such a detector, have proven themselves to be useful only for indicating the presence of ammonia and/or amino acid vapors in relatively high concentrations.

Indeed, this situation exists, notwithstanding Mallow's teaching that his chemical composition, when applied to selected surfaces as a paint, can serve as a passive detector for extremely low concentrations of vapor or liquid reactants, such as ammonia.

Specifically, tests were done by the applicant on detectors in which one of Mallow's compositions served as the indicator chemical, with this composition being sealed within the detector in such a way that it could not be activated by airborne chemicals from the atmosphere/outside environment. Rather, because of the manner in which the detector was attached to the test subject's body, the composition could only be activated by compounds released through the wearer's skin, thereby limiting the exposure of Mallow's composition to the constituents of human body odor. These tests showed no color changes in Mallow's compositions when they were exposed, for intervals of up to four hours at a time, to ammonia and amino acids at the concentrations at which they are found in human body odor.

Moreover, each of Mallow's compositions, once it has changed color as a result of exposure to sufficiently high concentrations of ammonia or other nitrogen-type compounds, is known to revert back to its original color (e.g., yellow) after a period of time. Consequently, valuable information may be lost before a user realizes that a spike in the release of ammonia or the like has occurred.

SUMMARY OF THE INVENTION

I have discovered when testing Mallow's compositions that not only did they fail to change color when they were exposed to the concentrations of odor-producing chemicals which are found in human body odor but also two of the solvents (butyl acetate and toluene) which Mallow included in each of his compositions attacked certain transparent, non-absorbent polymer films, otherwise suitable for use as window material in a visual detector, and actually dissolved these films.

I have further discovered that the failure of Mallow's compositions to change color is caused, in part, by the presence of ethyl cellulose which functions, in each of them, as a combination water insoluble binder and highly permeable membrane through which odor-producing gases, such as ammonia vapor, can pass. Unfortunately, the ethyl cellulose also acts to coat amorphous silica, a substrate for the dye bromophenol blue in these compositions, and in the process inhibits reaction between the odor-producing gases and the indicator chemical. Indeed, this reaction is slowed to the point that Mallow's compositions cannot be used as the indicator chemical in an odor detector in a hunting environment.

The present invention solves these problems by providing an improved detector which includes an indicator chemical consisting of a dry powder which reacts quickly, undergoing a color change, when it is exposed to nitrogen-containing compounds at extremely low concentrations, the dry powder being held in place within a detector packet which, when affixed to the outside of a hunter's clothing properly worn, is capable of trapping, with its indicator chemical, a portion of the odor-producing gases escaping through the hunter's clothing, without interference from such gases and/or other nitrogen-containing compounds generated by outside sources.

More specifically, there is provided a dry reactive chemical powder and a two-sided detector packet for holding it, the detector packet having an outer face which defines a first opening, a window fabricated of a transparent, nonabsorbent tape stretched across the first opening and affixed to the outer face forming an airtight seal with it, and an inner face which defines a through opening. The two sides of the detector packet are joined together along their contiguous outer edges so as to form a continuous airtight seal and define a centrally-located void fluidly connected to the through opening. Mounted within the detector packet is a thin layer, preferably measuring at most $1/10,000$th inch in thickness, of the dry reactive chemical powder. This thin layer is held in place, behind the window, by the adhesive backing of the tape which is stretched across the first opening-and is visible through the window. A nonhydroscopic filter media sheet permeable to gaseous, odor-producing chemicals, also mounted within the detector packet, covers the thin layer of dry reactive chemical powder in such a way that this thin layer is juxtaposed between the transparent, nonabsorbent tape and the filter media sheet and is accessible to such chemicals diffusing through the filter media sheet from the centrally-located void.

The dry reactive chemical powder itself is prepared by blending together, so as to form a slurry, only three substances: the solvent acetone, the dye bromophenol blue, and amorphous silica, the latter functioning both as a substrate for the dye and as a dye sensitizer, and then evaporating off the acetone, leaving, as a dry residue, a yellow powder, ready for use as an indicator chemical which permanently changes color whenever it adsorbs an extremely low threshold amount of gaseous ammonia or amino acids.

Accordingly, it is an advantageous feature of the present invention that an odor detector is provided which, when its inner face is adhesively affixed to the outside surface of odor eliminating clothing for hunters such as that developed by Sesselmann, gives a permanent visual indication that the concentrations of odor-producing chemicals escaping through said clothing are sufficiently high that the user's human body odor might be detectable by game animals.

A related advantageous feature of the invention is that an odor detector constructed in accordance with the present invention can be fabricated from relatively low cost materials, making practicable a "one time use only" visual detector which, once its indicator chemical has been activated to change its color, does not revert to its original color, thereby creating a permanent record which a hunter can use to decide whether sufficient human body odor has escaped from his clothing that he needs to take preventive action.

BRIEF DESCRIPTION OF THE DRAWINGS

FIG. 1 is a plan view of a partially finished frame of the detector packet according to the present invention, which shows a transparent, nonabsorbent tape affixed to an exterior surface of the frame and covering one of its openings;

FIG. 2 is a plan view of the partially finished frame according to FIG. 1, which shows the frame's other side and a dry reactive chemical powder added thereto, the latter being shown as a thin layer adhering to the adhesive backing side of the transparent, nonabsorbent tape;

FIG. 3 is a plan view of the partially finished frame according to FIG. 1, which shows the frame's other side and a filter media sheet added thereto, the latter covering the same opening as does the transparent, nonabsorbent tape but, unlike it, being affixed to the interior surface of the frame; the filter media sheet, in this view, obscuring the thin layer of dry reactive chemical powder which is juxtaposed between the filter media sheet and the tape;

FIG. 4 is a plan view of the two-sided detector packet according to the present invention, which shows its outer face and the opening therein sealed by the transparent, nonabsorbent tape, the tape forming a clear window through which the dry reactive chemical powder adhering to the tape's adhesive backing is visible; the finished frame having been constructed by folding the partially finished frame according to FIG. 2 so as to align the two openings in it;

FIG. 5 is a plan view of the two-sided detector packet according to the present invention, which shows its inner face and both a two-sided tape and a protective backing, the two-sided tape which is affixed to the frame being sandwiched between the frame and the protective backing, the two-sided tape and the protective backing being peeled back to expose a corner of the frame and a portion of a perforated plug formed in the two-sided tape, respectively; and FIG. 6 is a transverse cross-section, on an enlarged scale, taken along line 6-6 of FIG. 3.

DETAILED DESCRIPTION OF THE PREFERRED EMBODIMENT

Referring to the drawings, a body odor detection device according to the present invention is indicated generally by the reference numeral 10. The device 10 includes a generally planar dry chemistry unit 11 and a frame 21 which supports the chemistry unit.

The chemistry unit 11 comprises a strip of transparent, nonabsorbent tape 13, a thin layer of a dry reactive chemical powder 12, and at least one sheet 15 of a non-hydroscopic filter media. Affixed to the exterior surface of the frame 21 and forming a continuous airtight seal with a portion thereof which defines a view aperture 22, the tape strip 13 covers the latter opening. Partially embedded within an adhesive coating 14 backing the tape 13, the dry reactive chemical powder 12 is held in place within a window well surrounded by the peripheral edge of the opening 22 and a thin annular ring 28 which is mounted on the interior surface of the frame 21 (FIGS. 1, 2 and 6). Most of the particles of the dry reactive chemical powder 12 not adhered to the adhesive coating 14 are kept within the window well by the filtering action of the sheet 15; the latter element, generally centered on the view aperture 22, is bonded by adhesive to the interior surface of the frame 21 (FIG. 3).

Unfinished, the frame 21, which is fabricated from a sheet of pressed paper, plastic, metal or the like, resembles, in its shape, a pair of side-by-side rectangular forms from each of which a generally circular hole 22, 23 has been cut out (FIG. 1). Once the chemistry unit 11 is in place on the unfinished frame 21, it is then folded in such a way that the centers of the view aperture 22 and through opening 23, which is preferably about ⅛th inch greater in diameter than the view aperture, are generally aligned (FIGS. 4 and 5). Simultaneously, as the frame 21 is being so folded, the two newly-formed sides of its interior surface, precoated with adhesive, are pressed together, sealing their edges.

Assembly of the two-sided detector packet 10 is then complete except for the application, to the packet's inner face 30, of backing material such as a two-sided tape 31 with adhesive coatings 32, 33 and a protective covering 35. Prior to their being applied to the packet 10, both the two-sided tape 31 and the protective covering 35 are cut to size so that they can cover substantially the entire surface area of the inner face 30. A circular perforation 36 positioned in such a way that it can be centered over the through opening 23 and having a ⅛th inch greater diameter than the latter opening is also punched into the tape 31, forming a plug 34 which can be disengaged from the remainder of this tape (FIG. 5).

Immediately prior to use, the protective covering 35 is peeled off in order to expose the outer adhesive coating 33 so that the detector packet 10 can be sealed to a hunter's clothes. The orientation of the detector packet 10 is then such that the transparent, nonabsorbent tape 13 through which the dry reactive chemical powder 12 is visible faces away from the user.

During the process of peeling off the protective covering 35, the plug 34 stays attached to it, leaving the remainder of the two-sided tape 31 affixed to the inner face 30 and uncovering the through opening 23 so that odor-producing chemicals which escape from the outer surface of the hunter's clothes can diffuse into the packet 10 and come into contact with the dry chemistry unit 11. Moreover, in the event the level of exposure from odor-producing chemicals which so escape proves to be too low to trigger a permanent color change in the dry reactive chemical powder 12, the user has the option of reapplying the protective covering 35, with the plug 34 still attached, to the packet's inner face 30, thereby sealing off its through opening 23 so that the packet 10 can be stored for reuse.

The dry reactive chemical powder 12 of the present invention is prepared from a slurry which consists of only three substances: the solvent acetone, the dye bromophenol blue, and amorphous silica. Remaining structurally unchanged in the slurry, the amorphous silica, which in the preferred embodiment, exists in the form of powder granules in the 9 to 11 micron size range, readily absorbs the acetone and the bromophenol blue molecules dissolved it. Not only does the low viscosity of acetone allow it to penetrate these powder granules with their very small pore size but also it insures that the acetone evaporates quickly leaving little, if any, residual solvent to outgas from the dry reactive chemical powder 12. The acetone, which can be evaporated off the slurry at room temperature, leaves behind, as a dry residue, a yellow powder, which is believed to be the product of amorphous silica granules absorbing bromophenol blue molecules.

The ingredients and ranges of each ingredient in parts by weight for the slurry from which the dry reactive chemical powder 12 of the present invention is prepared are illustrated in Chart A hereinbelow:

CHART A

| Ingredients | Range (Parts by Weight) |
| --- | --- |
| Amorphous Silica | 26 to 40 |
| Bromophenol Blue | 0.01 to 0.19 |
| Acetone | 50 to 120 |

The following examples are presented to illustrate the composition of the slurry from which the dry reactive chemical powder 12 of the present invention is prepared in a more detailed manner:

EXAMPLE 1

| Ingredients | Quantity | Parts by Weight | Percentage by Weight |
| --- | --- | --- | --- |
| Amorphous Silica | 26 grams | 26 | 20.63% |
| Bromophenol Blue | 0.19 grain | 0.01 | 0.01% |
| Acetone | 100 grams | 100 | 79.3% |

EXAMPLE 2

| Ingredients | Quantity | Parts by Weight | Percentage by Weight |
| --- | --- | --- | --- |
| Amorphous Silica | 30 grams | 30 | 23.08% |
| Bromophenol Blue | 0.19 grain | 0.01 | 0.008% |
| Acetone | 100 grams | 100 | 76.92% |

EXAMPLE 3

| Ingredients | Quantity | Parts by Weight | Percentage by Weight |
| --- | --- | --- | --- |
| Amorphous Silica | 30 grams | 30 | 23.04% |
| Bromophenol Blue | 0.3 grain | 0.019 | 0.015% |
| Acetone | 100 grams | 100 | 76.91% |

EXAMPLE 4

| Ingredients | Quantity | Parts by Weight | Percentage by Weight |
| --- | --- | --- | --- |
| Amorphous Silica | 50 grams | 50 | 33.32% |
| Bromophenol Blue | 1.0 grain | 0.065 | 0.043% |
| Acetone | 100 grams | 100 | 66.64% |

EXAMPLE 5

| Ingredients | Quantity | Parts by Weight | Percentage by Weight |
| --- | --- | --- | --- |
| Amorphous Silica | 40 grams | 40 | 44.43% |
| Bromophenol Blue | 0.31 grain | 0.020 | 0.022% |
| Acetone | 50 grams | 50 | 55.54% |

As the applicant's tests have shown, the sensitivity of the dry reactive chemical powder 12 can be varied by varying the percentage of amorphous silica in the slurry. Specifically, when this percentage drops below approximately 18%, the dried reactive chemical powder 12 takes at least 3 hours to change color; and it may turn to only a yellow green, not a blue, or give no definite indication at all. On the other hand, when the percentage of amorphous silica in the slurry goes above 44% (as in Example 5 hereinabove), the powder 12 is too sensitive and turns an olive green with only minimal stimulus from outside sources such as atmospheric nitrogen. It is believed that when the percentage by weight of amorphous silica is around 35%, the dry reactive chemical powder 12 exhibits an optimum sensitivity for use in the detector packet 10, subject as it is to the time constraints of hunters.

Another critical factor which must be taken into account in selecting preferred embodiments of the powder 12 is the ratio between the quantity of bromophenol blue and the quantity of amorphous silica in the slurry. The applicant has found that the shelf life of the powder 12 is substantially enhanced when this ratio is maintained at approximately 0.01 grain of bromophenol blue to 1 gram of amorphous silica or higher ratios. In the case of Example 2, for instance, this ratio fell to only 0.006; and the powder 12 turned blue in less than 1 year. But in the case of Example 3, where the slurry from which the dried powder 12 was prepared closely resembles that in Example 2 except for the fact that this critical ratio was 0.01 instead of 0.006, the dried powder has thus far had a shelf life in excess of 1-½ years. If one were to select the composition of the slurry from which the dry reactive chemical powder 12 is prepared on the basis of stability/extended shelf life alone, EXAMPLE 6 would be a preferred candidate:

EXAMPLE 6

| Ingredients | Quantity | Parts by Weight | Percentage by Weight |
|---|---|---|---|
| Amorphous Silica | 20 grams | 20 | 16.66% |
| Bromophenol Blue | 0.2 grain | 0.013 | 0.01% |
| Acetone | 100 grams | 100 | 83.3% |

Indeed, this slurry is so stable that the amorphous silica granules settle out in such a way as to facilitate pouring off the excess acetone; but because the percentage by weight of amorphous silica is less than 18%, any dried reactive chemical powder prepared from it would take too long to change color to be of practical value in the detector packet 10, especially under the time constraints hunting imposes.

Yet another factor which can significantly alter the rate at which the dry reactive chemical powder 12 changes color is the depth of the powder layer through which nitrogen type compounds must diffuse before they can activate bromophenol blue molecules within the viewing range of a would-be observer. In the case of the detector packet 10, the applicant has found that the greater the depth of the layer of dry reactive chemical powder 12 in the dry chemistry unit 11, the longer this color change takes before it is observable through the view aperture 22. In the preferred embodiment, the thin layer of powder 12 has a depth of approximately $1/10{,}000$th inch.

It is to be understood that any adhesives employed to bond together components of the dry chemistry unit 11, as well as adhesives to secure the unit 11 to the frame 21 and bond together elements of the frame itself, must be free of any traces of ammonia or nitrogen type compounds. Otherwise, the dry reactive chemical powder 12 immediately turns color, e.g., blue. In the preferred embodiment, the transparent, nonabsorbent tape 13 is a clear packaging tape with an adhesive backing found, by trial and error, to be free of any nitrogen type compounds including ammonia. The same has been found to be true for the annular ring 28 which is preferably fabricated from a clear vinyl film.

The amorphous silica used in preparing the dry reactive chemical powder 12 can be purchased from Sygma Aldrich and is categorized as having a Davisil Grade 710, with a size range of 9.5 to 11 microns. Between $1/10$ grain and 2 grains of the dry reactive chemical powder 12 is used in each dry chemistry unit 11.

The non-hydroscopic filter media sheet 15 is preferably a polyester fiber woven fabric which is two layers thick. This double layered filter blocks about 90% of the amorphous silica granules which otherwise would migrate out of the thin layer of dry reactive chemical powder 12 disposed contiguous with the adhesive coating 14 on the tape 13. The manufacturer of the polyester fiber woven fabric used in the sheet 15 is Hoppe's. Alternately, a filter media made of glass and having a 5 micron pore size, which is available commercially from Fisher Scientific, can be utilized for the sheet 15.

The two-sided detector packet 10 is preferably square shaped and measures, by way of example, two inches on a side, with the view aperture 22 and the through opening 23 having diameters of 1 inch and 1-⅛ inch, respectively. In addition, the circular perforation in the two-sided tape 31 preferably leaves a 1-¼ inch hole in this tape when the plug 34, which is approximately 1-⅛ inch in diameter, is pulled out.

In use, the dry reactive chemical powder 12 in the packet 10 turns from yellow to light green to blue depending upon the concentrations of nitrogen type compounds such as ammonia and amino acids in the vapors to which the powder is exposed. When the level of human odor escaping from a hunter's odor absorbing clothing turns the detector blue, it is believed that game animals are able to smell the presence of a human. The powder 12 in the detector packet 10 is extremely sensitive and can detect vapors of ammonia or amino acids, as well as atmospheric nitrogen, when they are present in concentrations of parts per billion. Indeed, once the dry chemical unit 11 has been exposed to nitrogen type compounds which are present in concentrations in the parts per billion range, the color of the dry reactive chemical powder 12 changes from yellow to blue. Moreover, the powder 12 in the unit 11 holds the blue color so that the hunter has a chance to know that his body odor is escaping through his odor eliminating clothes. Unlike the prior art, the powder 12 in the unit 11 will not revert back to its original yellow color.

In summary, the improved device according to the present invention not only can detect extremely low levels of airborne amino acids, ammonia vapor or other gaseous nitrogen-type compounds but also is limited to a single "blue" exposure. That is, once the dry reactive chemical powder 12 has been exposed, the powder does not revert back to its unexposed state, thereby giving the user the earliest possible indication that his body odor eliminating clothing is at or near its saturation limit and a breakthrough of odor-producing chemicals has occurred or is about to occur.

It is claimed:

1. A device adapted to be worn on the exterior of hunters' odor absorbing clothing, which comprises:
    (a) a dry reactive chemical powder having granules which undergo a color change when exposed to gaseous nitrogen-containing compounds such as ammonia and amino acids;
    (b) a two-sided detector packet, the packet having front and rear sides, the front side defining a view aperture and the rear side defining a through opening;
    (c) a transparent, nonabsorbent tape with an adhesive backing, the tape, which is stretched across the view aperture, being positioned between the atmosphere and the dry reactive chemical powder, a thin layer of the powder being affixed to a portion of the tape's adhesive backing, said portion generally spanning the view aperture, the thin layer so affixed being visible through the tape and kept out of contact with the atmosphere during use;
    (d) means, including a nonhydroscopic filter media sheet, for generally blocking migration of granules of the dry reactive chemical powder away from the tape's adhesive backing and towards the through opening, the filter media sheet, in use, being positioned between the powder and the odor absorbing clothing; and
    (e) wherein said thin layer and any powder held between it and the filter media sheet are sufficiently porous that the gaseous nitrogen-containing compounds, once they have traversed the filter media sheet, diffuse rapidly through the powder until they react with powder granules disposed contiguous with the transparent tape.

2. The device according to claim 1, wherein the dry reactive chemical powder is further characterized as consisting essentially of two substances: the dye bromophenol blue and amorphous silica, the powder being prepared by blending these two substances together with the solvent acetone to form a slurry in which the percentage by weight of amorphous silica therein is at least approximately 18 percent and then drying the slurry by evaporating off the acetone until little, if any, residual solvent remains, leaving said powder in the form of a dry yellow powder residue which can be activated by atmospheric nitrogen as well as by gaseous ammonia and amino acids, the powder, when so activated, undergoing a color change which, in those situations in which the powder is exposed to human body odor, generally occurs within an exposure time of three hours or less.

3. A device adapted to be worn on the exterior of hunters' odor absorbing clothing, which comprises:
  (a) a dry reactive chemical powder having granules which undergo a color change when exposed to gaseous nitrogen-containing compounds such as ammonia and amino acids;
  (b) a two-sided detector packet, the packet having front and rear sides which define a view aperture and a through opening, respectively; the view aperture and the through opening being generally circular in transverse cross-section, the view aperture and the through opening, in assembled relation, being arrayed concentrically about an imaginary straight line which passes through their respective centers;
  (c) a transparent, nonabsorbent tape with an adhesive backing, the tape, which is stretched across the view aperture, being positioned between the atmosphere and the dry reactive chemical powder, a thin layer of the powder being affixed to a portion of the tape's adhesive backing, said portion generally spanning the view aperture, the thin layer so affixed being visible through the tape;
  (d) means, including a nonhydroscopic filter media sheet affixed to the packet's interior surfaces in such a way that the sheet spans both the view aperture and the through opening, for generally blocking migration of granules of the dry reactive chemical powder away from the tape's adhesive backing and towards the through opening, the filter media sheet, in use, being positioned between the powder and the odor absorbing clothing; and
  (e) wherein said thin layer and any powder held between it and the filter media sheet are sufficiently porous that the gaseous nitrogen-containing compounds, once they have traversed the filter media sheet, diffuse rapidly through the powder until they react with powder granules disposed contiguous with the transparent tape.

4. A device adapted to be worn on the exterior of hunters' odor eliminating clothing, which comprises:
  (a) an indicator chemical in the form of a dry reactive chemical powder which is sensitive to atmospheric nitrogen as well as to extremely low concentrations of other nitrogen-containing compounds such as ammonia and amino acids, the indicator chemical undergoing an irreversible color change once it has been exposed to a threshold level of such nitrogen-containing compounds, the threshold level being sufficiently low that said compounds, when present in concentrations at which they are typically found in human body odor, trigger the irreversible color change;
  (b) a detector packet defining a view aperture and a through opening, the packet being affixed, in use, to the odor eliminating clothing;
  (c) means, including a transparent material which covers the view aperture, for mounting a thin layer of the indicator contiguous therewith, the thin layer being sealed within the packet in such a way that, during use, it is kept out of contact with the atmosphere but viewable through the view aperture and fluidly connected, via the through opening, to a portion of said clothing's exterior; and
  (d) wherein the indicator chemical, once exposed to said threshold level of nitrogen-containing compounds, provides a permanent record of its exposure to human body odor which has escaped from said portion of the clothing's exterior.

* * * * *